United States Patent
Zhang et al.

(10) Patent No.: US 12,290,289 B1
(45) Date of Patent: May 6, 2025

(54) ELASTIC INTRAMEDULLARY FIXATION DEVICE

(71) Applicant: The Fourth Medical Center of the Chinese People's Liberation Army General Hospital, Beijing (CN)

(72) Inventors: Licheng Zhang, Beijing (CN); Peifu Tang, Beijing (CN); Xiang Cui, Beijing (CN); Chi Ma, Beijing (CN); Houchen Lv, Beijing (CN); Jia Li, Beijing (CN); Hua Chen, Beijing (CN)

(73) Assignee: The Fourth Medical Center of the Chinese People's Liberation Army General Hospital, Beijing (CN)

( * ) Notice: Subject to any disclaimer, the term of this patent is extended or adjusted under 35 U.S.C. 154(b) by 0 days.

(21) Appl. No.: 19/017,237

(22) Filed: Jan. 10, 2025

(30) Foreign Application Priority Data

Mar. 25, 2024 (CN) .......................... 202410344282.0

(51) Int. Cl.
*A61B 17/72* (2006.01)

(52) U.S. Cl.
CPC ...... *A61B 17/7208* (2013.01); *A61B 17/7233* (2013.01)

(58) Field of Classification Search
CPC .......................... A61B 17/7208; A61B 17/7233
See application file for complete search history.

(56) References Cited

U.S. PATENT DOCUMENTS

| | | | |
|---|---|---|---|
| 4,776,330 A | 10/1988 | Chapman et al. | |
| 5,976,137 A | 11/1999 | Mayer | |
| 2014/0114312 A1* | 4/2014 | Krause | A61B 17/864 606/62 |
| 2014/0309363 A1* | 10/2014 | Morita | C08K 3/013 526/194 |
| 2020/0054372 A1* | 2/2020 | Stinson | A61B 17/7208 |
| 2021/0378827 A1 | 12/2021 | Pascale et al. | |
| 2023/0404636 A1* | 12/2023 | Whittaker | A61B 17/8685 |

FOREIGN PATENT DOCUMENTS

CN         117257430 A     12/2023

* cited by examiner

*Primary Examiner* — Tessa M Matthews

(57) ABSTRACT

An elastic intramedullary fixation device includes a serpentine frame and a shell, the inner surface of the shell is rotatably connected with a locking rod, one end of the locking rod is inserted with a key rod, one end of the shell is inserted with a clamping rod, the outer surfaces of the clamping rod and the key rod are sleeved with a connecting sleeve, the outer surfaces of the clamping rod and the key rod are provided with a connecting component, and the surfaces of the clamping rod and the shell are provided with a self-locking component. By configuring a connecting component and a self-locking component, the connecting component not only allows for the adjustment of the positional relationship between the key rod and the clamping rod, but also enables engagement with the locking component, thereby enhancing the stability of the connection between the clamping plate and the shell.

9 Claims, 12 Drawing Sheets

ELASTIC INTRAMEDULLARY FIXATION DEVICE

CROSS-REFERENCE TO RELATED APPLICATIONS

This application claims priority to Chinese Patent Application No. 202410344282.0 with a filing date of Mar. 25, 2024. The content of the aforementioned application, including any intervening amendments thereto, is incorporated herein by reference.

TECHNICAL FIELD

The present disclosure relates to the technical field of fracture repair, in particular to an elastic intramedullary fixation device.

BACKGROUND ART

Fractures may occur in straight bones such as femur or curved bones such as pelvis. Repairing fractures usually involves two steps: fracture reduction and fracture fixation. Reduction is a step to reposition a fracture by minimizing the distance between bone fragments and anatomically aligning the bone to minimize the deformity after healing. There are surgical and non-surgical reduction methods. Fixation is a step to keep fracture fragments mechanically stable and close to each other to promote bone healing, which may take several weeks or longer, depending on the fracture type, the bone type and the general health condition of the injured patient.

For example, Chinese Patent Publication CN109862840A discloses an intramedullary fixation device with a shape-locking junction, and discloses an implantable device for fixing curved bones and a method for using the device. Implantable devices can switch between a flexible state and a rigid state using a shape-locking part. The implantable device further includes a main body and a distal bone junction. In the flexible state, the device can be inserted along and conform to the curved path, while in the rigid state, the device can support the mechanical load required to stabilize the fracture.

Although the above-mentioned intramedullary fixation device can switch between the rigid and flexible states by manipulating the shape-locking mechanism, the limiting structure of the fixation device and the matching structure of the external implant tool are provided at the end of the shape-locking mechanism, which makes the end structure of the whole device large. Therefore, when the operator fixes the device into the human medullary, it is necessary to form a through hole at the end of the bone that is larger than the main structure, so as to ensure the shape-locking mechanism can smoothly engage with the intramedullary cavity to achieve fixation. It takes more time to form a larger through hole, and the operator needs to pay attention to the thickness of the bone at all times in the process of forming a large through hole, which will lead to the low efficiency of the intramedullary fixation device in the placing process.

The operational process for implanting the intramedullary fixation device described above into the patient's bone is as follows: A guide wire and a hole-forming device are used to form a through hole in the patient's bone. The hole-forming device is then removed from the bone, and the guide wire is used to drive the main body into the bone through an external implantation tool. Afterward, the guide wire is withdrawn, and a key is inserted through the external implantation tool and fixed into the key-receiving part at the end of the shape-locking mechanism. The key is rotated, and the internal compression component is used to compress and lock the fibers, thereby achieving the conversion of the main body from a flexible state to a rigid state. Once the key is used, it must be withdrawn from the external implantation tool, and finally, the external implantation tool is removed from the end of the shape-locking mechanism, completing the device placement process. During this operation, the operator must first withdraw the guide wire after the main body is placed, and then insert the key into the external implantation tool. Once the key is used, the key and the external implantation tool must be withdrawn in sequence. This repetitive process is time-consuming. Therefore, in order to improve the efficiency of the implant placement, the present disclosure provides an elastic intramedullary fixation device to meet the demand.

SUMMARY

The present disclosure provides an elastic intramedullary fixation device. By configuring a connecting component and a self-locking component, the connecting component not only allows for the adjustment of the positional relationship between the key rod and the clamping rod, but also enables engagement with the locking component, thereby enhancing the stability of the connection between the clamping plate and the shell. By configuring a locking component, the device not only enables a self-locking function between the clamping rod and the shell, but also allows for the engagement with the connecting component, so that once the position of the implant is determined, the locking process of the serpentine frame structure is more efficient. After the serpentine frame structure is locked, the key rod and the clamping rod can be more easily removed from the patient's bone. The above configuration can resolve the issues of low operational efficiency during the locking of the serpentine frame structure in the process of implant placement, as well as low efficiency in removing the implant tool after the serpentine frame structure has been locked.

In order to solve the above technical problems, the present disclosure provides the following technical solutions.

An elastic intramedullary fixation device includes a serpentine frame and a shell, wherein one end of the serpentine frame is provided with a drill bit, inner surfaces of the serpentine frame and the shell are inserted with fibers, the inner surface of the shell is rotatably connected with a locking rod, one end of the locking rod is inserted with a key rod, one end of the key rod is fixedly connected with a key head, one end of the shell is inserted with a clamping rod, outer surfaces of the clamping rod and the key rod are sleeved with a connecting sleeve, and a guide wire hole for the insertion of a guide wire is formed in inner surfaces of the drill bit, the serpentine frame, the locking rod and of the key rod; the outer surfaces of the clamping rod and the key rod are provided with a connecting component, the connecting component is configured to fix a relative position between the clamping rod and the key rod, and the connecting component is respectively connected with the clamping rod and the key rod; and the surfaces of the clamping rod and the shell are provided with a self-locking component, the self-locking component is configured to lock a relative position between the clamping rod and the shell, and the self-locking component is respectively connected with the clamping rod and the shell.

Optionally, the inner surface of the shell is provided with a limiting groove, the outer surface of the locking rod is fixedly connected with a limiting block adapted to the limiting groove, and the end surface of the locking rod is provided with a receiving key adapted to the key head.

Optionally, the connecting component includes a connecting sleeve sleeved on the outer surface of the key rod, and the inner surface of the connecting sleeve is fixedly connected with a connecting piece. The surfaces of the key rod and the clamping rod are provided with first grooves, and the connecting piece can be clamped into the first grooves of the key rod and the clamping rod at the same time. The outer surface of the clamping rod is provided with a second groove, and the outer surface of the key rod is provided with a third groove corresponding to the second groove. When the key rod moves until the third groove is aligned with the second groove, the connecting piece can be clamped into the second groove and the third groove at the same time.

Optionally, the inner surface of the connecting sleeve is fixedly connected with an arc-shaped elastic sheet group, and the connecting pieces and the connecting sleeve are fixedly connected through the arc-shaped elastic sheet group, and three connecting pieces are provided.

Optionally, an outer surface of the connecting sleeve is provided with an arc-shaped groove, the outer surface of the connecting sleeve is provided with anti-skid lines, and the outer surface of the clamping rod is fixedly connected with a stop piece.

Optionally, the self-locking component includes a clamping plate fixedly connected with one end of the clamping rod, the surface of the shell is provided with a clamping groove adapted to the clamping plate, and the inner surface of the shell is fixedly connected with a self-locking elastic sheet.

Optionally, the inner surface of the shell is provided with a tapered groove structure, and an end of the key rod is provided with a tapered structure.

Optionally, one end of the clamping rod is fixedly connected with an end plate, and a surface of the end plate is fixedly connected with an arc-shaped plate.

Optionally, a surface of the self-locking elastic sheet is fixedly connected with a self-locking clamping block, a surface of the clamping plate is provided with a self-locking clamping groove, and the inner surface of the shell is provided with an avoidance groove.

Optionally, the end plate, the arc-shaped plate and the clamping plates are all curved structures with inherent elasticity, and three clamping plates and three self-locking elastic sheets are provided.

Compared with the prior art, the present disclosure has at least the following beneficial effects:

In the above solutions, the overall structure of the implant tends to be flat and smooth by configuring the connecting component and the self-locking component, so that the operator does not need to form through holes with different sizes during the implantation of the implant into the bone.

The connecting component not only allows for the adjustment of the positional relationship between the key rod and the clamping rod, but also enables engagement with the locking component, thereby enhancing the stability of the connection between the clamping plate and the shell.

By configuring a locking component, the device not only enables a self-locking function between the clamping rod and the shell, but also allows for the engagement with the connecting component, so that once the position of the implant is determined, the locking process of the serpentine frame structure is more efficient. After the serpentine frame structure is locked, the key rod and the clamping rod can be more easily removed from the patient's bone.

BRIEF DESCRIPTION OF DRAWINGS

The accompanying drawings, which are incorporated herein and constitute a part of the specification, illustrate embodiments of the present disclosure and, together with the specification, further serve to explain the principles of the present disclosure and to enable those skilled in the relevant art to implement and use the present disclosure.

Figure 1:
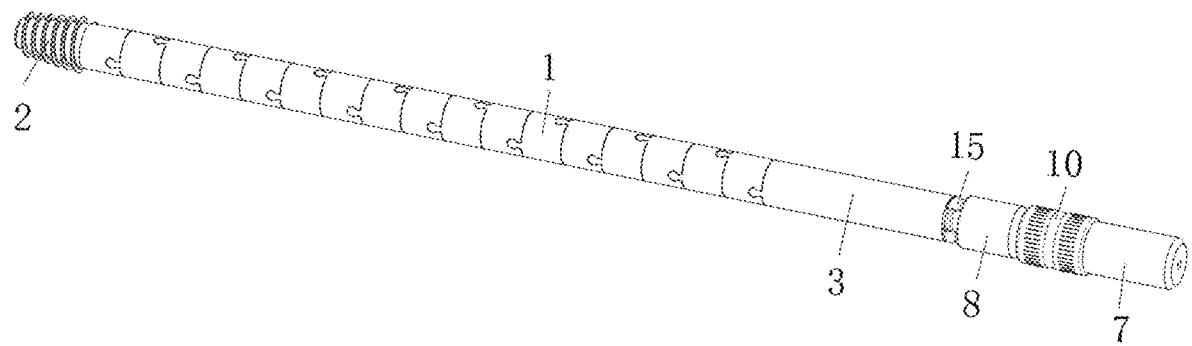
FIG. 1 is a perspective view of an elastic intramedullary fixation device.
Figure 2:
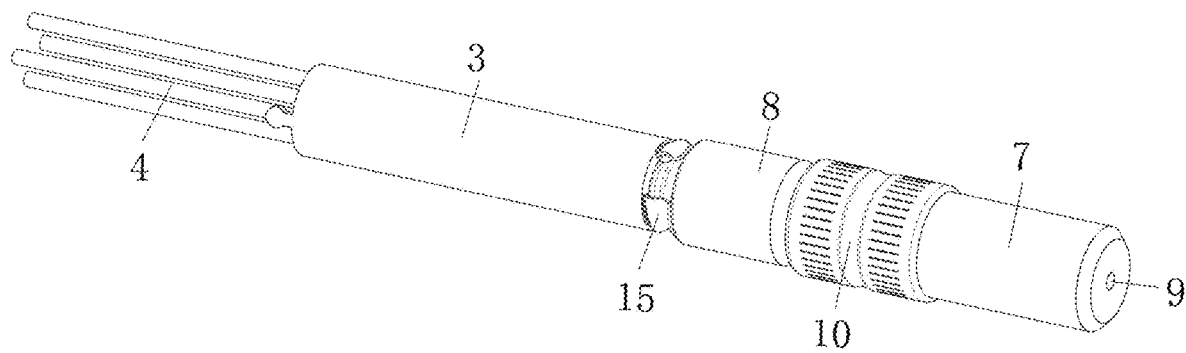
FIG. 2 is an enlarged perspective view of the assembly at the junction of the shell, the key rod and the clamping rod.

[Reference numerals] 1. Serpentine frame; 2. Drill bit; 3. Shell; 4. Fibers; 5. Locking rod; 6. Receiving key; 7. Key rod; 8. Clamping rod; 9. Guide wire hole; 10. Connecting sleeve; 11. Limiting groove; 12. Limiting block; 13. Key head; 14. End plate; 15. Arc-shaped plate; 16. clamping plate; 17. Clamping groove; 18. Self-locking elastic sheet; 19. Self-locking clamping block; 20. Self-locking clamping groove; 21. Avoidance groove; 22. Arc-shaped elastic sheet group; 23. Connecting piece; 24. First groove; 25. Stop piece; 26. Second groove; 27. Third groove.

As shown in the figures, in order to clearly implement the structure of the embodiments of the present disclosure, specific structures and devices are marked in the figures, but this is only for schematic needs, and it is not intended to limit the present disclosure to the specific structures, devices and environments. According to specific needs, those ordinarily skilled in the art may adjust or modify these devices and environments, and the adjustment or modification shall still fall within the scope of the appended Claims.

DETAILED DESCRIPTION

An elastic intramedullary fixation device provided by the present disclosure will be described in detail in combination with the accompanying drawings and specific embodiments. At the same time, it is explained here that in order to make the embodiments more detailed, the following embodiments are the best and preferred embodiments. For some well-known technologies, those skilled in the art can also adopt other alternative ways to implement them. Moreover, the drawings are only intended to describe embodiments in more detail and are not intended to specifically limit the present disclosure.

It should be pointed out that references to "one embodiment", "an embodiment", "exemplary embodiment" and "some embodiments" in the specification indicate that the described embodiments may include a specific feature, structure or characteristic, but not every embodiment necessarily includes the specific features, structures or characteristics. In addition, when describing a specific feature, structure or characteristic in conjunction with an embodiment, it should be within the knowledge of those skilled in the relevant art to implement such feature, structure or characteristic in conjunction with other embodiments (whether explicitly described or not).

Generally, terms can be understood at least in part from the use in the context. For example, depending at least in part on the context, the term "one or more" as used herein can be used to describe any feature, structure or characteristic in the singular sense, or can be used to describe a combination of features, structures or characteristics in the plural sense. In addition, the term 'based' may be understood as not necessarily intended to convey a set of exclusive factors, but depending on the context, may allow for other factors that are not explicitly described.

It can be understood that the meanings of "on", "above" and "over" in the present disclosure should be interpreted in the widest way, so that "on" not only means "directly on" something, but also includes "on" something with intervening features or layers, and "above" or "over" not only means "above" or "over" something, but also includes the meaning of "above" or "over" something without intervening features or layers.

In addition, space-related terms such as "under", "below", "at the lower part", "above" and "at the upper part" can be used to describe the relationship between one element or feature and another element or feature or more elements or features, as shown in the drawings. Space-related terms are intended to cover different orientations in the use or operation of a device other than those depicted in the drawings. A device can be oriented in other ways, and spatially related descriptors used herein can be similarly interpreted accordingly.

As shown in FIGS. 1 to 12, the embodiment of the present disclosure provides an elastic intramedullary fixation device, which includes a serpentine frame 1 and a shell 3. One end of the serpentine frame 1 is provided with a drill bit 2, and the inner surfaces of both the serpentine frame 1 and the shell 3 are inserted with fibers 4. The inner surface of the shell 3 is rotatably connected with a locking rod 5. One end of the locking rod 5 is inserted with a key rod 7, and one end of the key rod 7 is fixedly connected to a key head 13. One end of the shell 3 is inserted with a clamping rod 8, and the clamping rod 8 and the key rod 7 are provided with a connecting sleeve 10 on their outer surfaces. The inner surfaces of the drill bit 2, the serpentine frame 1, the locking rod 5, and the key rod 7 are provided with a guide wire hole 9 for the insertion of a guide wire. During the process of implanting the drill bit 2 and the serpentine frame 1 into the patient's medullary cavity, the guide wire is inserted through the guide wire hole 9 to guide the drill bit 2 and the serpentine frame 1. The use of the guide wire can improve the efficiency of implanting the drill bit 2 and the serpentine frame 1. Outer surfaces of the clamping rod 8 and the key rod 7 are provided with a connecting component. The connecting component is used to fix the relative position between the clamping rod 8 and the key rod 7. The connecting component is connected to both the clamping rod 8 and the key rod 7. The surfaces of the clamping rod 8 and the shell 3 are provided with a self-locking component. The self-locking component is used to lock the relative position between the clamping rod 8 and the shell 3. The self-locking component is connected with both the clamping rod 8 and the shell 3.

Figure 3:
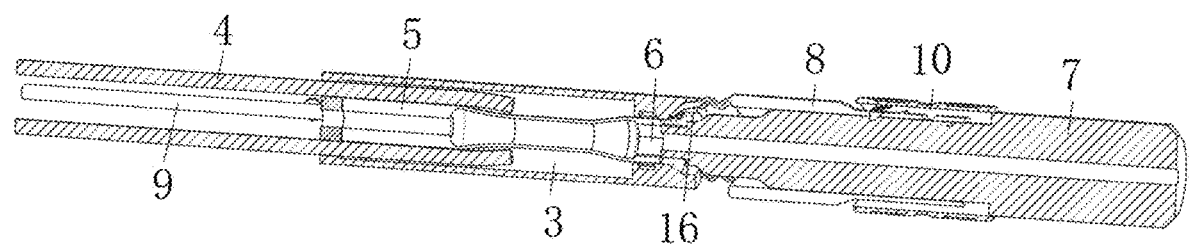
FIG. 3 is a cross-sectional perspective view of the elastic intramedullary fixation device.
Figure 4:
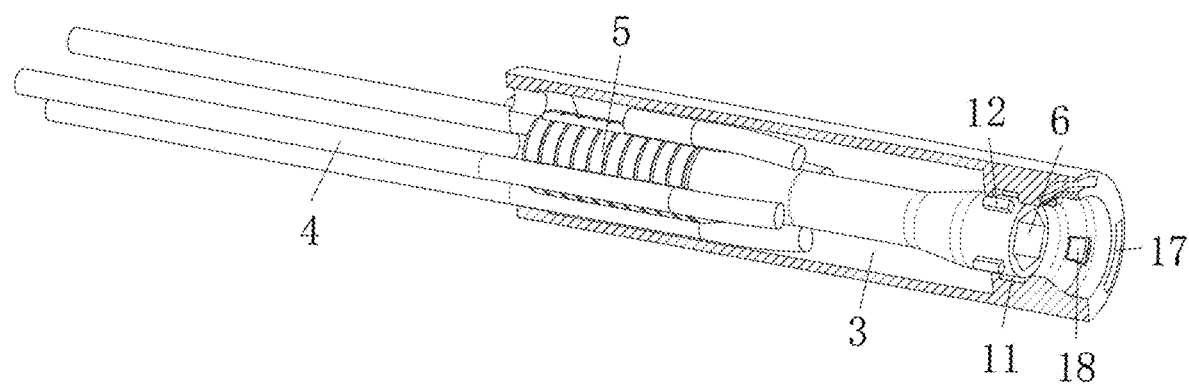
FIG. 4 is a cross-sectional perspective view of the assembly at the junction of the shell and the locking rod.
Figure 5:
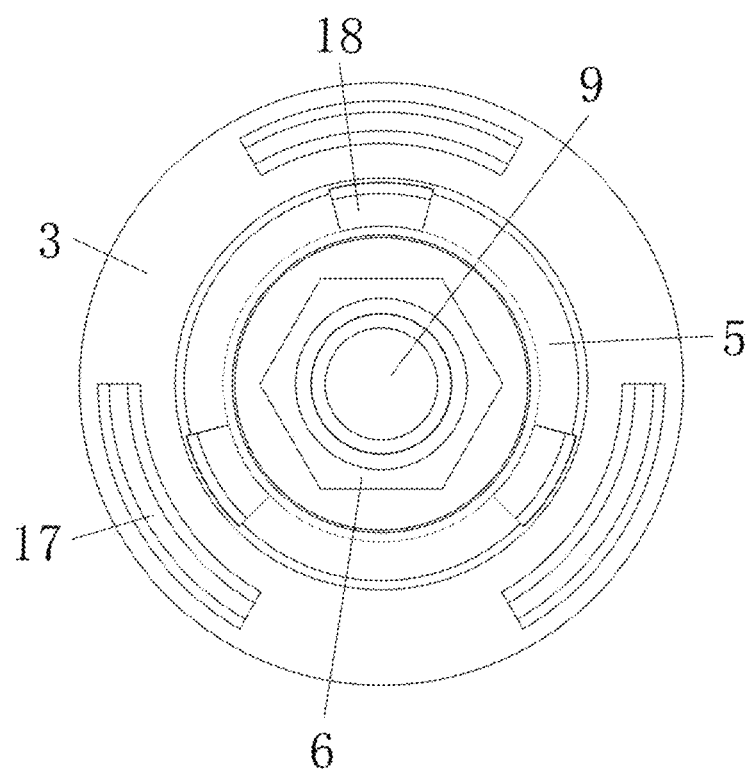
FIG. 5 is a partial view of the end face of the shell.
Figure 6:
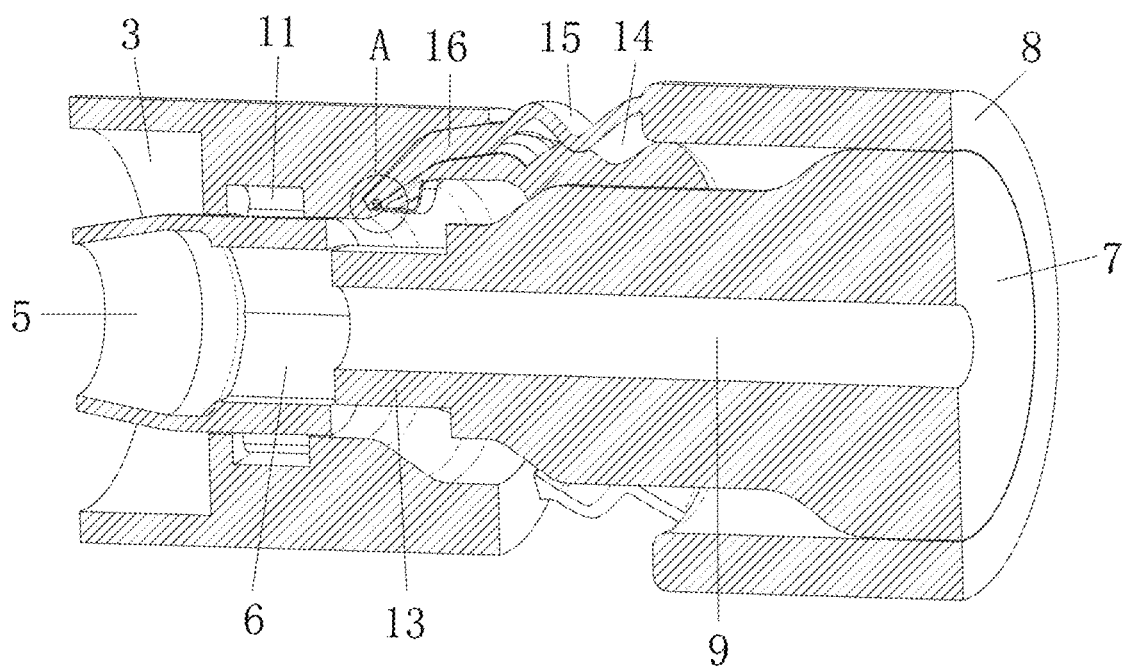
FIG. 6 is a cross-sectional perspective view of the assembly at the self-locking component.

As shown in FIGS. 3, 4 and 6, the inner surface of the shell 3 is provided with a limiting groove 11, the outer surface of the locking rod 5 is fixedly connected with a limiting block 12 adapted to the limiting groove 11, and the end surface of the locking rod 5 is provided with a receiving key 6 adapted to a key head 13.

As shown in FIGS. 9 to 12, the connecting component includes a connecting sleeve 10 sleeved on the outer surface of the key rod 7, and a connecting piece 23 is fixedly connected with the inner surface of the connecting sleeve 10. The surfaces of the key rod 7 and the clamping rod 8 are provided with first grooves 24, the connecting piece 23 can be clamped into the first grooves 24 of the key rod 7 and the clamping rod 8 at the same time, and the outer surface of the clamping rod 8 is provided with a second groove 26. The outer surface of the key rod 7 is provided with a third groove 27 corresponding to the second groove 26. When the key rod 7 moves until the third groove 27 is aligned with the second groove 26, the connecting piece 23 can be clamped into the second groove 26 and the third groove 27 at the same time.

Figure 12:
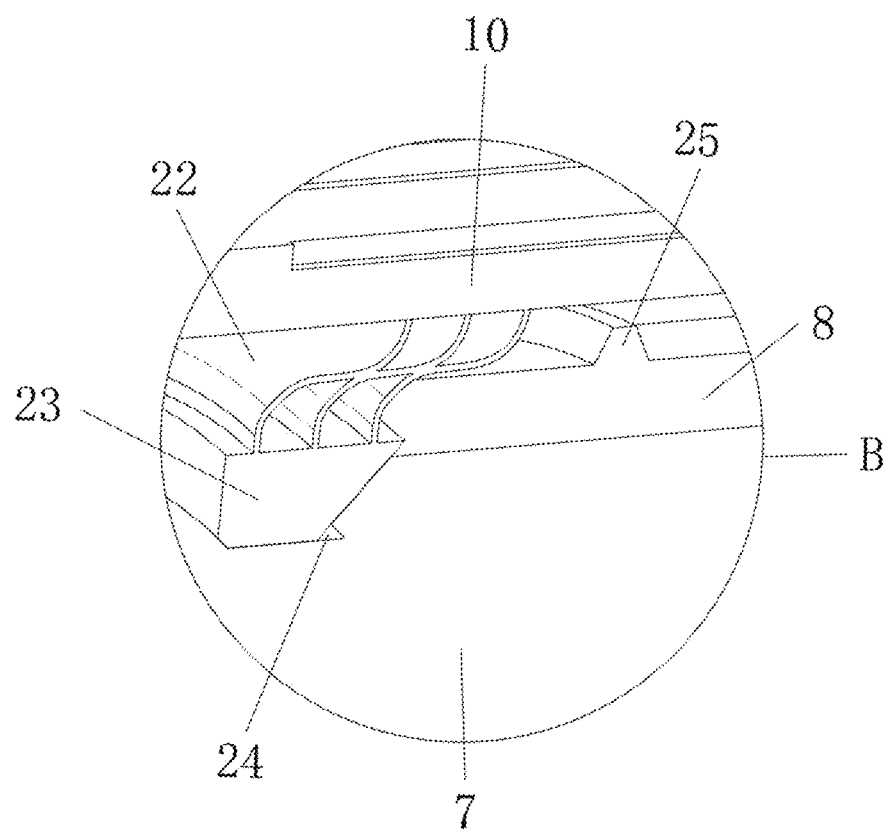
FIG. 12 is an enlarged partial view at location B in FIG. 11.

As shown in FIG. 12, the inner surface of the connecting sleeve 10 is fixedly connected with an arc-shaped elastic sheet group 22, and the connecting piece 23 is fixedly connected with the connecting sleeve 10 through the arc-shaped elastic sheet group 22, and three connecting pieces 23 are provided.

As shown in FIGS. 9 to 12, the outer surface of the connecting sleeve 10 is provided with an arc-shaped groove, the outer surface of the connecting sleeve 10 is provided with anti-skid lines, and the outer surface of the clamping rod 8 is fixedly connected with a stop piece 25. At the initial state, the connecting piece 23 will be clamped into the first groove 24 under the elastic action of the arc-shaped elastic sheet group 22, and when the operator slides the connecting sleeve 10 toward the end of the key rod 7, the connecting sleeve 10 will give the connecting piece 23 a thrust. When this thrust acts on the surface of the connecting piece 23, it will first push the connecting piece 23 to slide, because the surface of the connecting piece 23 is provided with an inclined structure with self-guidance, so with the inclined structure of the first groove 24, the connecting piece 23 will slide out of the first groove 24 and reach the stop piece 25, and the arc-shaped elastic sheet group 22 will deform and contract when the connecting piece 23 slides out of the first groove 24, and when it reaches the stop piece 25, under the elastic action of the arc-shaped elastic sheet group 22, the connecting piece 23 will be resisted by the stop piece 25 and cannot slide any more. At this time, under the action of the stop piece 25, the connecting piece 23 will give the operator a stop signal, which will remind the operator that the connecting piece 23 has slipped out of the first groove 24 and is located at the front end of the stop piece 25, which means that the key rod 7 and the clamping rod 8 have escaped from the limit. At this time, the key rod 7 and the clamping rod 8 can slide with each other. After receiving this signal, the operator needs to push the key rod 7 to push the key head 13 into the receiving key 6. During the pushing process of the key rod 7, the third groove 27 will slide to the inner surface of the second groove 26. After the key head 13 is connected with the receiving key 6, the operator needs to continue to slide the connecting sleeve 10 with a little force. During the sliding process of the connecting sleeve 10, the connecting piece 23 will drive the arc-shaped elastic sheet group 22 to continuously contract under the action of the stop piece 25. Until the moment when the connecting piece 23 completely slides over the stop piece 25, the arc-shaped elastic sheet group 22 restores its deformation and pushes the connecting piece 23 back to the outer surface of the clamping rod 8. At this time, the connecting piece 23, in conjunction with the arc-shaped elastic sheet group 22, provides the operator with a vibration signal, which will remind the staff that the connecting piece 23 has passed through the stop piece 25. At this time, if the connecting sleeve 10 continues to slide, the connecting piece 23 will enter the second groove 26 and the third groove 27. The operator keeps sliding the connecting sleeve 10, and the connecting piece 23 will be clamped into the second groove 26 and the third groove 27 under the action of the arc-shaped elastic sheet group 22. Because the second groove 26 and the third groove 27 are longer than the first groove 24, the second groove 26 and the third groove 27 can only provide a one-way limit for the connecting piece 23. At this time, under the limiting action of the second groove 26 and the third groove 27, the key rod 7 can rotate on the inner surface of the clamping rod 8, but cannot slide, in this way, the operator can achieve the rotation of the locking rod 5 to rotate by rotating the key rod 7.

As shown in FIGS. 4 to 8, the self-locking component includes a clamping plate 16 fixedly connected with one end of the clamping rod 8, a clamping groove 17 adapted to the clamping plate 16 is provided on the surface of the shell 3, and a self-locking elastic sheet 18 is fixedly connected with the inner surface of the shell 3.

Figure 7:
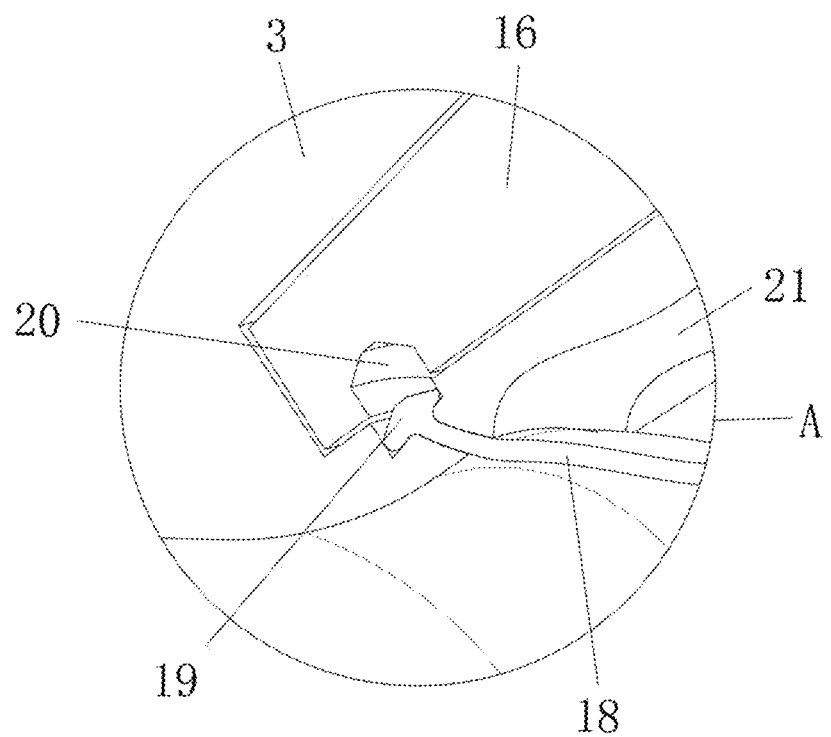
FIG. 7 is an enlarged partial view at location A in FIG. 6.
Figure 8:
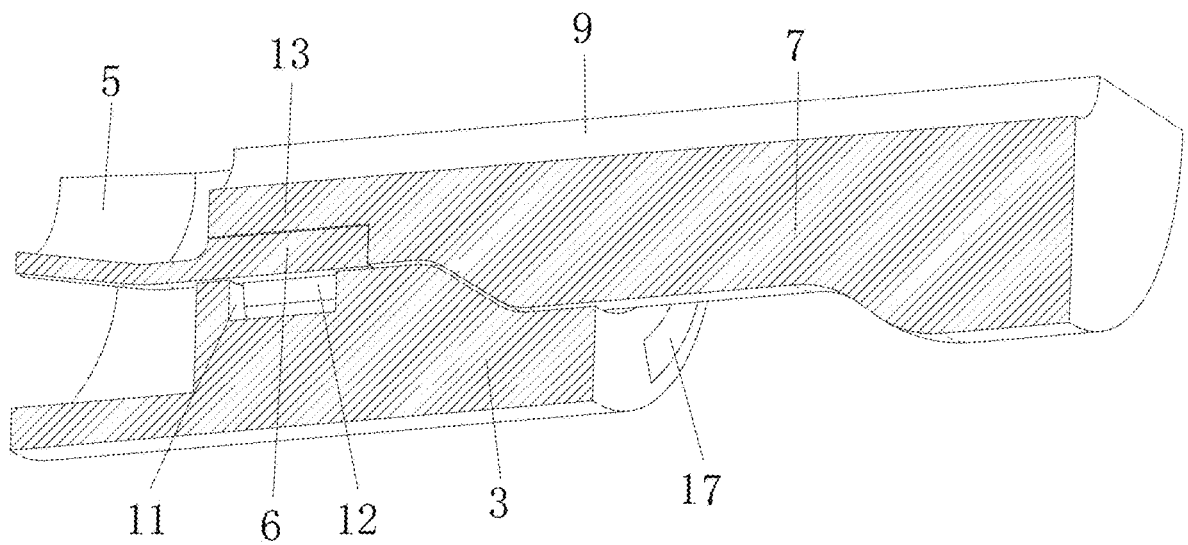
FIG. 8 is a cross-sectional perspective view of the assembly where the key head is inserted into the receiving key.

As shown in FIGS. 6 and 7, one end of the clamping rod 8 is fixedly connected with an end plate 14, and the surface of the end plate 14 is fixedly connected with an arc-shaped plate 15. The surface of the self-locking elastic sheet 18 is fixedly connected with a self-locking clamping block 19. The surface of the clamping plate 16 is provided with a self-locking clamping groove 20. The inner surface of the shell 3 is provided with an avoidance groove 21 for accommodating and limiting the deformed self-locking elastic sheet 18.

As shown in FIGS. 4 to 8, the inner surface of the shell 3 is provided with a tapered groove structure, and the end of the key rod 7 is provided with a tapered structure. During the push-in process of the key rod 7, the key head 13 will be inserted into the receiving key 6 naturally, and at the same time, the tapered structure at the end of the key rod 7 will be matched with the notch of the tapered structure on the inner surface of the shell 3. This configuration has two advantages. Firstly, when the key rod 7 is pushed into the shell 3, the tapered structure can guide and limit the key rod 7, so as to achieve the self-locking effect and allow the key head 13 to be accurately inserted into the receiving key 6. Secondly, the tapered structure allows the key head 13 to self-lock the clamping plate 16 with the locking component when it is inserted into the receiving key 6. The self-locking elastic sheet 18 on the inner surface of the shell 3 is arranged in the tapered groove. When the key rod 7 is pushed into the shell 3, the key rod 7 will compress the self-locking elastic sheet 18 to deform, and the self-locking clamping block 19 at one end will be conveniently clamped into the self-locking clamping groove 20 on the surface of the clamping plate 16 during the squeezing process. Thus, under the continuous compression of the key rod 7, the self-locking clamping block 19 will be continuously clamped in the self-locking clamping groove 20. This arrangement has the advantage that when there is only one-way limit between the key rod 7 and the clamping rod 8, the stability of the connection between the clamping plate 16 and the shell 3 can be further improved by the arrangement of the self-locking component, so as to prevent the position and angle of the implant from deviating during the shape-locking of the serpentine frame 1.

Figure 9:
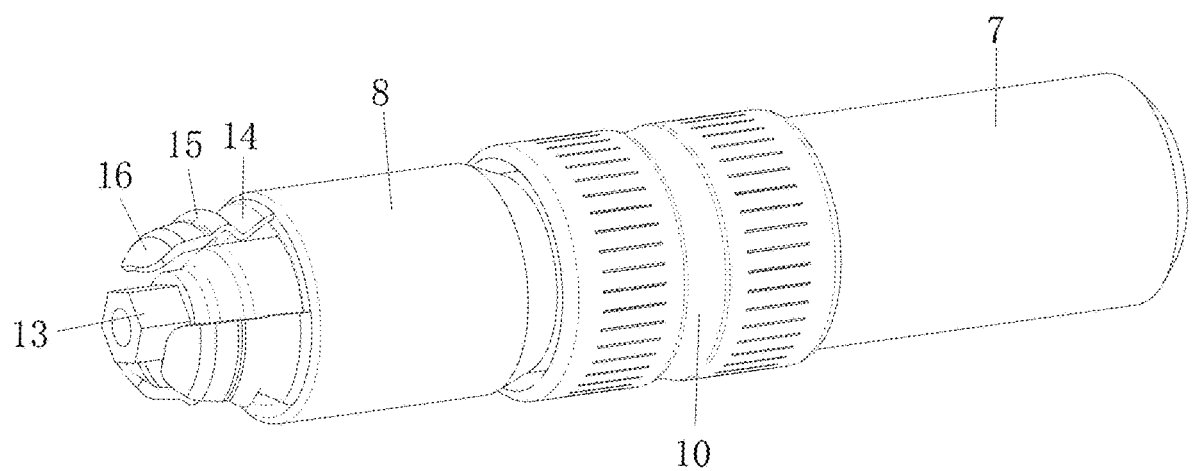
FIG. 9 is an enlarged perspective view of the assembly at the junction of the key rod, the clamping rod and the connecting sleeve.
Figure 10:
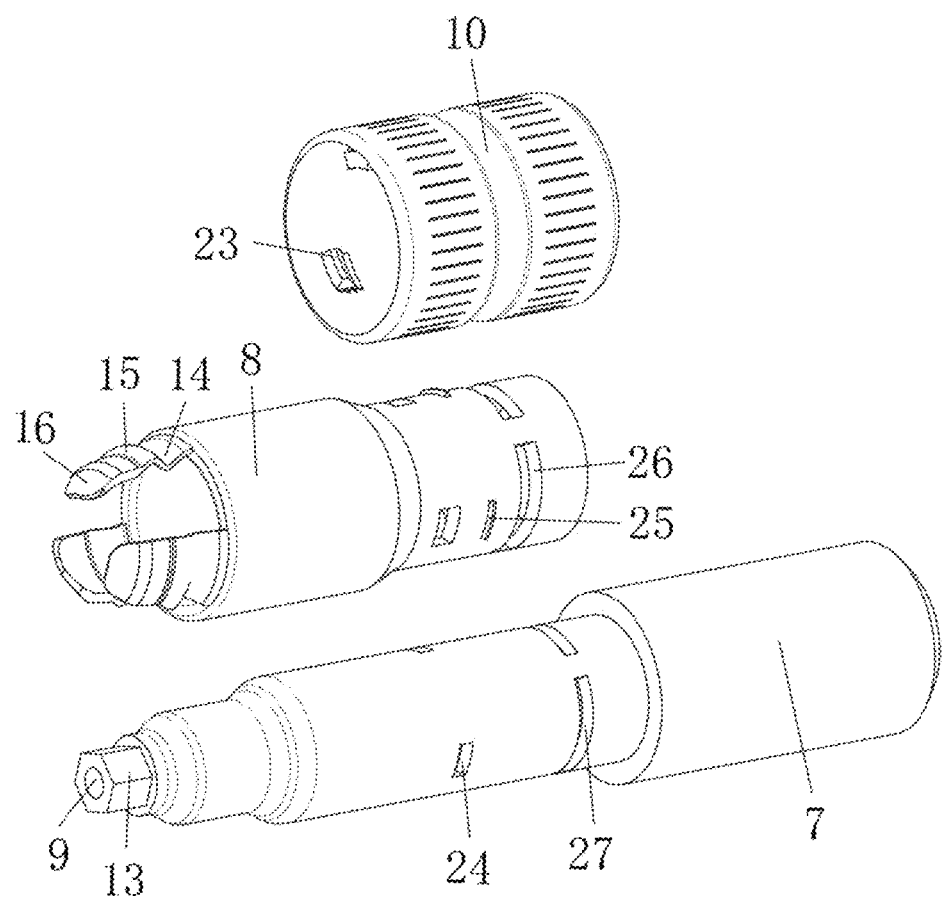
FIG. 10 is an exploded perspective view of the assembly at the junction of the key rod, the clamping rod and the connecting sleeve.
Figure 11:
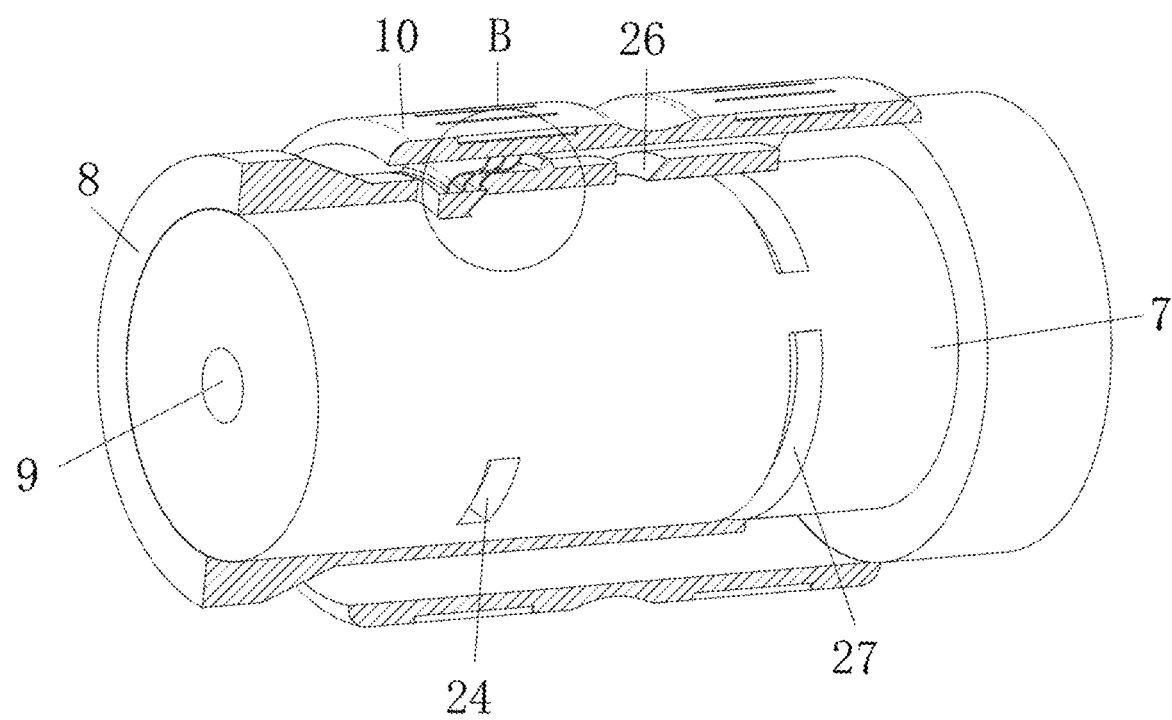
FIG. 11 is a cross-sectional perspective view of the assembly at the connecting component.

As shown in FIGS. 9 and 10, the end plate 14, the arc-shaped plate 15 and the clamping plate 16 are all curved structures with self-elastic functions, and three clamping plates 16 and three self-locking elastic sheets 18 are provided. This arrangement has three advantages. Firstly, under the elastic effect of the curved surface structure of the end plate 14, after the clamping plate 16 is inserted into the clamping groove 17, an inward clamping force can naturally be formed between the clamping plate 16 and the clamping groove 17; because the clamping groove 17 itself can play a role in limiting the clamping plate 16, and with the limiting effect of the elastic clamping force of the upper end plate 14, the cooperation between the clamping plate 16 and the shell 3 can be more firm and stable. Secondly, the flexibility between the end plate 14 and the clamping plate 16 can be improved under the elastic effect of the curved structure of the arc-shaped plate 15; because the operator needs to twist and hammer the serpentine frame 1 during the process of driving the implant into the bone, the elastic structure of the arc-shaped plate 15 can buffer and absorb the torsional force and impact force during this process, thus preventing the phenomenon of detachment and misalignment between the clamping plate 16 and the clamping groove 17 during the process of driving the implant into the bone. Thirdly, because the clamping plate 16 has its own curved surface structure, and the clamping groove 17 is matched with the curved surface bending shape of the clamping plate 16, after the clamping plate 16 is inserted into the clamping groove 17, the clamping plate 16 and the clamping groove 17 can form an automatic locking function under the limiting effect of the curved surface structure. This arrangement, combined with the arrangement of the end plate 14 and the curved plate 15, can make the clamping plate 16 have better stability.

According to the technical solutions provided by the present disclosure, by arranging the self-locking component and the connecting component, when in use, firstly, a through hole is formed in a patient's bone by using a guide wire and a hole-forming device, and after the through hole is formed, the hole-forming device is taken out; secondly, a clamping rod is fixed at the end of the shell by using a clamping plate, and then an implant is driven into the bone with the through hole; and finally, the key rod and the clamping rod are separated from each other by using the connecting component, and then the key rod is pushed to insert the key head into the receiving key after the key rod and the clamping rod are separated from the limit. When the key head is inserted, the self-locking component locks the relative position between the shell and the clamping plate, and the key rod and the clamping rod will be reconnected by the connecting component. After the key head and the receiving key are inserted, the operator rotates the key rod, which drives the locking rod to squeeze and lock the fibers during the rotation of the key rod. At this time, the serpentine frame changes from a flexible state to a rigid state. After the shape of the serpentine frame is fixed, the operator pulls the key rod and the guide wire synchronously to take the key rod, the guide wire and the clamping rod out of the shell together.

Before the operator drives the implant into the bone, it is necessary to fix the clamping rod on the surface of the shell with a clamping plate. The clamping plate is fixed at the end of the clamping rod through an end plate and an arc-shaped plate. The end plate, the arc-shaped plate and the clamping plate are all curved structures with inherent elasticity. This arrangement has three advantages. Firstly, under the elastic action of the end plate's curved surface structure, when the clamping plate is inserted into the clamping groove, a natural inward clamping force is generated between the clamping plate and the clamping groove. Since the clamping groove itself provides a limiting function for the clamping plate, combined with the limiting effect of the elastic clamping force from the end plate, this ensures a firmer and more stable fit between the clamping plate and the shell. Secondly, under the elastic action of the curved plate's surface structure, the resilience between the end plate and the clamping plate is enhanced. During the process of implanting the device into the bone, where the operator needs to twist and hammer the serpentine frame, the elastic structure of the curved plate can buffer and absorb the torsional and impact forces. This helps prevent detachment or misalignment between the clamping plate and the clamping groove during the implantation process. Thirdly, as the clamping plate itself has a curved surface structure, and the curvature of the clamping groove matches that of the clamping plate, when the clamping plate is inserted into the clamping groove, the limiting action of the curved surface structure enables an automatic locking function between the clamping plate and the clamping groove. This configuration, combined with the end plate and the curved plate structure, enhances the overall stability of the clamping plate.

When the operator drives the implant into the bone, the connecting piece inside the connecting sleeve is clamped in the first groove on the surfaces of the key rod and the clamping rod, so that the key rod and the clamping rod can be limited in two directions under the limiting action of the connecting piece, and the key rod and the clamping rod can neither slide nor rotate. At this time, the operator can exert force on the shell and the serpentine frame by using the key rod, and good fixation can be maintained between the key rod and the clamping rod whether rotating or hammering the implant into the bone.

After the operator inserts the implant into the bone, it is necessary to use the locking rod to compress and lock the fibers. At this point, the operator must use the connecting component to adjust the positional relationship between the key rod and the clamping rod. In the initial state, the connecting piece will engage with the first groove under the elastic force of the arc-shaped elastic sheet group. When the operator slides the connecting sleeve towards the key rod end, the connecting sleeve will apply a force to the connecting piece. This force, when acting on the surface of the connecting piece, will first push the connecting piece to slide. Since the surface of the connecting piece is designed with a self-guiding inclined structure, in conjunction with the inclined structure of the first groove, the connecting piece will slide out of the first groove and reach the stop piece. During this sliding process, the arc-shaped elastic sheet group will deform and contract. When reaching the stop piece, the connecting piece will be blocked by the stop piece due to the elastic force of the arc-shaped elastic sheet group, preventing further sliding. At this time, under the action of the stop piece, the connecting piece will signal the operator to stop. This signal informs the operator that the connecting piece has slid out of the first groove and is now at the front end of the stop piece, indicating that the key rod and the clamping rod are no longer limited and can now move relative to each other. After receiving this signal, the operator must push the key rod to insert the key head into the receiving key. During this process, the third groove will slide along the inner surface of the second groove. Once the key head is fully connected with the receiving key, the operator must apply slight additional force to continue sliding the connecting sleeve. As the connecting sleeve slides, the connecting piece will drive the arc-shaped elastic sheet group to continue contracting under the action of the stop piece. This continues until the connecting piece completely slides past the stop piece. At this time, the arc-shaped elastic sheet group will return to its original shape and force the connecting piece back to the outer surface of the clamping rod. At this time, the connecting piece, in conjunction with the arc-shaped elastic sheet group, will provide a vibration signal to the operator, indicating that the connecting piece has passed through the stop piece. If the operator continues to slide the connecting sleeve, the connecting piece will enter both the second groove and the third groove. As the operator continues to slide the connecting sleeve, the connecting piece will engage with both the second groove and the third groove under the action of the arc-shaped elastic sheet group. Since the second groove and the third groove are longer than the first groove, this design ensures that the second groove and the third groove can only provide a one-way limit for the connecting piece. At this point, under the limitation of the second groove and the third groove, the key rod can rotate on the inner surface of the clamping rod, but cannot slide. This allows the operator to rotate the key rod to drive the locking rod to rotate.

In the process of pushing the key rod, the key head will be inserted into the receiving key naturally. At the same time, the tapered structure at the end of the key rod will be matched with the notch of the tapered structure on the inner surface of the shell, which has two advantages. Firstly, the tapered structure can guide and limit the key rod during the process of pushing the key rod into the shell, thus realizing the self-locking effect and allowing the key head to be inserted into the receiving key accurately. Secondly, with the arrangement of the tapered structure, the key head can be inserted into the process of receiving the key and cooperate with the locking assembly to self-lock the clamping plate, so that the self-locking elastic sheet on the inner surface of the shell is arranged in the tapered groove. When the key rod is pushed into the shell, the key rod will compress the self-locking elastic sheet to deform, and the self-locking clamping block at one end of the self-locking elastic sheet will be naturally stuck in the self-locking slot on the surface of the clamping plate during the compression process, so that the self-locking clamping block will be continuously stuck in the self-locking slot under the continuous compression of the key rod. The advantage of this arrangement is that when there is only one-way limit between the key rod and the clamping rod, the arrangement of the self-locking component can further improve the stability of the connection between the clamping plate and the shell, thus preventing the position and angle of the implant from shifting during the shape locking of the serpentine frame.

After the shape of the serpentine frame is fixed, the operator needs to take out the guide wire, the key rod and the clamping rod from the surface of the implant. At this time, the operator only needs to pull out the guide wire and the key rod synchronously, and the key head will be taken out from the receiving key during the process of pulling out the key rod. At the same time, under the limiting action of the connecting sleeve, when the key rod is pulled out, the clamping rod surface will also generate pulling power, and when the clamping rod surface generates pulling force, the clamping plate will not be separated from the clamping groove for the first time. Instead, the arc-shaped plate and the end plate are simply deformed. In this process, the tapered structure at the end of the key rod will reduce the pressure on the self-locking elastic sheet in the shell, so the self-locking elastic sheet will recover deformation under its own elasticity and drive the self-locking clamping block to separate from the self-locking clamping groove on the surface of the clamping plate. After the self-locking is released, the clamping plate will also be smoothly separated from the surface of the shell, and then it will be taken out of the bone together with the key rod and the guide wire. In this process, the operator does not need to perform any redundant operations and only needs to pull the key rod and the guide wire outwards.

The present disclosure encompasses any alternatives, modifications, equivalent methods and solutions made within the essence and scope of the present disclosure. In order to make the public have a thorough understanding of the present disclosure, specific details are set forth in the preferred embodiments of the present disclosure, and those skilled in the art can fully understand the present disclosure without the description of these details. Additionally, in order to avoid unnecessary confusion regarding the substance of the present disclosure, well-known methods, processes, procedures, components, circuits, etc., are not described in detail.

The above descriptions are merely illustrative of the preferred embodiments of the present disclosure. It should be noted that various modifications and variations may be made by those ordinarily skilled in the art without departing from the principles of the present disclosure, and such modifications and variations are also intended to fall within the scope of the present disclosure.

What is claimed is:

1. An elastic intramedullary fixation device, comprising a serpentine frame and a shell, wherein one end of the serpentine frame is provided with a drill bit, fibers are inserted into an inner surface of the serpentine frame and an inner surface of the shell respectively, the inner surface of the shell is rotatably connected with a locking rod, a key rod is inserted into one end of the locking rod, one end of the key rod is fixedly connected with a key head, a clamping rod is inserted into one end of the shell, outer surfaces of the clamping rod and the key rod are sleeved with a connecting sleeve, and a guide wire hole is defined in inner surfaces of the drill bit, the serpentine frame, the locking rod and the key rod respectively;

the outer surfaces of the clamping rod and the key rod are provided with a connecting component, the connecting component is configured to fix a relative position between the clamping rod and the key rod, and the connecting component is respectively connected with the clamping rod and the key rod;

surfaces of the clamping rod and the shell are provided with a self-locking component, the self-locking component is configured to lock a relative position between the clamping rod and the shell, and the self-locking component is respectively connected with the clamping rod and the shell;

the connecting component comprises the connecting sleeve sleeved on the outer surface of the key rod, an inner surface of the connecting sleeve is fixedly connected with a connecting piece, surfaces of the key rod and the clamping rod are provided with a first groove, the outer surface of the clamping rod is provided with a second groove, and the outer surface of the key rod is provided with a third groove; and the inner surface of the connecting sleeve is fixedly connected with an arc-shaped elastic sheet group, and the connecting piece and the connecting sleeve are fixedly connected through the arc-shaped elastic sheet group; a surface of the connecting piece is provided with an inclined structure with self-guidance; and the outer surface of the clamping rod is fixedly connected with a stop piece.

2. The elastic intramedullary fixation device according to claim 1, wherein the inner surface of the shell is provided with a limiting groove, an outer surface of the locking rod is fixedly connected with a limiting piece, and a surface of the locking rod is provided with a receiving key.

3. The elastic intramedullary fixation device according to claim 1, wherein three connecting pieces are provided.

4. The elastic intramedullary fixation device according to claim 1, wherein an outer surface of the connecting sleeve is provided with an arc-shaped groove, and the outer surface of the connecting sleeve is provided with anti-skid lines.

5. The elastic intramedullary fixation device according to claim 1, wherein the self-locking component comprises a clamping plate fixedly connected with one end of the clamping rod, a surface of the shell is provided with a clamping groove, and the inner surface of the shell is fixedly connected with a self-locking elastic sheet.

6. The elastic intramedullary fixation device according to claim 5, wherein the inner surface of the shell is provided with a tapered groove structure, and an end of the key rod is provided with a tapered structure.

7. The elastic intramedullary fixation device according to claim 5, wherein one end of the clamping rod is fixedly connected with an end plate, and a surface of the end plate is fixedly connected with an arc-shaped plate.

8. The elastic intramedullary fixation device according to claim 7, wherein the end plate, the arc-shaped plate and the clamping plate are all curved structures with inherent elasticity, and three clamping plates and three self-locking elastic sheets are provided.

9. The elastic intramedullary fixation device according to claim 5, wherein a surface of the self-locking elastic sheet is fixedly connected with a self-locking clamping piece, a surface of the clamping plate is provided with a self-locking clamping groove, and the inner surface of the shell is provided with an avoidance groove.

* * * * *